(12) United States Patent
Wang

(10) Patent No.: US 12,144,740 B2
(45) Date of Patent: *Nov. 19, 2024

(54) EXPANDABLE MOTION PRESERVATION SPACER

(71) Applicant: GLOBUS MEDICAL, INC., Audubon, PA (US)

(72) Inventor: Wenhai Wang, Wayne, PA (US)

(73) Assignee: Globus Medical Inc., Audubon, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/450,785

(22) Filed: Aug. 16, 2023

(65) Prior Publication Data

US 2023/0390075 A1 Dec. 7, 2023

Related U.S. Application Data

(63) Continuation of application No. 17/583,470, filed on Jan. 25, 2022, now Pat. No. 11,759,328, which is a continuation of application No. 16/563,084, filed on Sep. 6, 2019, now Pat. No. 11,259,933.

(51) Int. Cl.
*A61F 2/44* (2006.01)
*A61F 2/30* (2006.01)

(52) U.S. Cl.
CPC .......... *A61F 2/441* (2013.01); *A61F 2/30771* (2013.01); *A61F 2/4425* (2013.01); *A61F 2002/3082* (2013.01)

(58) Field of Classification Search
CPC ................................ A61F 2/44–447
See application file for complete search history.

(56) References Cited

U.S. PATENT DOCUMENTS

| | | | |
|---|---|---|---|
| 3,867,728 A * | 2/1975 | Stubstad | A61F 2/442 |
| | | | 128/DIG. 21 |
| 4,349,921 A | 9/1982 | Kuntz | |
| 4,599,086 A | 7/1986 | Doty | |
| 4,863,476 A | 9/1989 | Shepperd | |
| 4,863,477 A | 9/1989 | Monson | |
| 5,123,926 A | 6/1992 | Pisharodi | |
| 5,290,312 A | 3/1994 | Kojimoto et al. | |

(Continued)

FOREIGN PATENT DOCUMENTS

| | | |
|---|---|---|
| CA | 2088066 A1 | 1/1992 |
| DE | 4012622 C1 | 7/1991 |

(Continued)

*Primary Examiner* — Matthew J Lawson

(57) ABSTRACT

Embodiments are directed to an expandable spacer for insertion between two adjacent bony structures or two adjacent joint surfaces, and more particularly relate to an expandable spacer for insertion into the void remaining in the intervertebral space. Embodiments may include an expandable spacer comprising a first endplate; a second endplate spaced from the first endplate; and one or more bags disposed between the first endplate and the second endplate that couple the first endplate to the second endplate. The one or more bags may be configured to receive a filler material to expand the expandable spacer from an initial position having a first height to an expanded position having a second height, wherein the second height is greater than the first height.

16 Claims, 6 Drawing Sheets

(56) References Cited

U.S. PATENT DOCUMENTS

| | | |
|---|---|---|
| 5,306,310 A | 4/1994 | Siebels |
| 5,375,823 A | 12/1994 | Navas |
| 5,390,683 A | 2/1995 | Pisharodi |
| 5,522,899 A | 6/1996 | Michelson |
| 5,534,030 A | 7/1996 | Navarro et al. |
| 5,554,191 A | 9/1996 | Lahille et al. |
| 5,571,192 A | 11/1996 | Schonhoffer |
| 5,645,596 A | 7/1997 | Kim |
| 5,653,763 A | 8/1997 | Errico et al. |
| 5,665,122 A | 9/1997 | Kambin |
| 5,676,701 A | 10/1997 | Yuan et al. |
| 6,039,761 A | 3/2000 | Li et al. |
| 6,045,579 A | 4/2000 | Hochschuler et al. |
| 6,080,193 A | 6/2000 | Hochschuler et al. |
| 6,099,531 A | 8/2000 | Bonutti |
| 6,126,689 A | 10/2000 | Brett |
| 6,176,882 B1 | 1/2001 | Biedermann et al. |
| 6,258,125 B1 | 7/2001 | Paul et al. |
| 6,558,423 B1 | 5/2003 | Michelson |
| 6,562,074 B2 | 5/2003 | Gerbec et al. |
| 6,576,016 B1 | 6/2003 | Hochschuler et al. |
| 6,554,863 B2 | 8/2003 | Paul et al. |
| 6,641,614 B1 | 11/2003 | Wagner et al. |
| 6,648,917 B2 | 11/2003 | Gerbec et al. |
| 6,666,891 B2 | 12/2003 | Boehm, Jr. et al. |
| 6,692,495 B1 | 2/2004 | Zacouto |
| 6,706,070 B1 | 3/2004 | Wagner et al. |
| 6,752,832 B2 | 6/2004 | Ulrich |
| 6,814,756 B1 | 11/2004 | Michelson |
| 6,830,589 B2 | 12/2004 | Erickson |
| 6,849,093 B2 | 2/2005 | Michelson |
| 6,852,129 B2 | 2/2005 | Gerbec et al. |
| 6,863,673 B2 | 3/2005 | Gerbec et al. |
| 6,881,228 B2 | 4/2005 | Zdeblick et al. |
| 7,018,415 B1 | 3/2006 | McKay |
| 7,070,598 B2 | 7/2006 | Lim et al. |
| 7,204,853 B2 | 4/2007 | Gordon |
| 7,217,291 B2 | 5/2007 | Zucherman et al. |
| 7,282,063 B2 | 10/2007 | Cohen et al. |
| 7,316,714 B2 | 1/2008 | Gordon |
| 7,473,276 B2 | 1/2009 | Aebi et al. |
| 7,547,325 B2 | 6/2009 | Biedermann et al. |
| 7,621,953 B2 | 11/2009 | Braddock, Jr. et al. |
| 7,641,693 B2 | 1/2010 | Gutlin et al. |
| 7,682,396 B2 | 3/2010 | Beaurain et al. |
| 7,749,270 B2 | 7/2010 | Peterman |
| 7,753,958 B2 | 7/2010 | Gordon |
| 7,771,473 B2 | 8/2010 | Thramann |
| 7,780,732 B2 | 8/2010 | Abernathie |
| 7,799,081 B2 | 9/2010 | McKinley |
| 7,815,683 B2 | 10/2010 | Melkent et al. |
| 7,837,734 B2 | 11/2010 | Zucherman et al. |
| 7,875,078 B2 | 1/2011 | Wysocki et al. |
| 7,901,409 B2 | 3/2011 | Canaveral et al. |
| 7,909,869 B2 | 3/2011 | Gordon |
| 7,951,199 B2 | 5/2011 | Miller |
| 7,985,256 B2 | 7/2011 | Grotz et al. |
| 8,062,375 B2 | 11/2011 | Glerum |
| 8,070,813 B2 | 12/2011 | Grotz et al. |
| 8,123,810 B2 | 2/2012 | Gordon |
| 8,137,405 B2 | 3/2012 | Kostuik et al. |
| 8,192,495 B2 | 6/2012 | Simpson et al. |
| 8,303,663 B2 | 11/2012 | Jimenez et al. |
| 8,377,140 B2 | 2/2013 | DeFalco et al. |
| 8,394,129 B2 | 3/2013 | Lopez et al. |
| 8,394,143 B2 | 3/2013 | Grotz et al. |
| 8,435,296 B2 | 5/2013 | Kadaba et al. |
| 8,454,695 B2 | 6/2013 | Grotz et al. |
| 8,647,386 B2 | 2/2014 | Gordon |
| 8,696,751 B2 | 4/2014 | Ashley et al. |
| 8,771,360 B2 | 7/2014 | Jimenez et al. |
| 8,894,710 B2 | 11/2014 | Simpson et al. |
| 8,932,355 B2 | 1/2015 | Grotz et al. |
| 8,940,049 B1 | 1/2015 | JImenez et al. |
| 8,956,413 B2 | 2/2015 | Ashley et al. |
| 8,992,620 B2 | 3/2015 | Ashley et al. |
| 9,028,550 B2 | 5/2015 | Shulock et al. |
| 9,358,125 B2 | 6/2016 | Jimenez et al. |
| 9,532,883 B2 | 1/2017 | McLuen et al. |
| 9,622,878 B2 | 4/2017 | Grotz |
| 2002/0045945 A1 | 4/2002 | Liu |
| 2002/0068976 A1 | 6/2002 | Jackson |
| 2002/0068977 A1 | 6/2002 | Jackson |
| 2003/0045939 A1* | 3/2003 | Casutt ............... A61F 2/442 623/17.15 |
| 2003/0176926 A1 | 9/2003 | Boehm et al. |
| 2004/0030387 A1 | 2/2004 | Landry et al. |
| 2004/0049271 A1 | 3/2004 | Biedermann |
| 2004/0054412 A1 | 3/2004 | Gerbec et al. |
| 2004/0087947 A1 | 5/2004 | Lim et al. |
| 2004/0153065 A1 | 8/2004 | Lim |
| 2004/0249462 A1* | 12/2004 | Huang ............... A61F 2/4425 623/17.13 |
| 2005/0021041 A1 | 1/2005 | Michelson |
| 2005/0021145 A1 | 1/2005 | de Villiers et al. |
| 2005/0033432 A1 | 2/2005 | Gordon |
| 2005/0080422 A1 | 4/2005 | Otte et al. |
| 2005/0113916 A1 | 5/2005 | Branch |
| 2005/0149188 A1 | 7/2005 | Cook |
| 2005/0171541 A1 | 8/2005 | Boehm |
| 2005/0197702 A1* | 9/2005 | Coppes ............... A61F 2/441 623/17.13 |
| 2005/0228500 A1* | 10/2005 | Kim ............... A61F 2/4611 623/17.13 |
| 2005/0251258 A1 | 11/2005 | Jackson |
| 2005/0273171 A1 | 12/2005 | Gordon |
| 2005/0273174 A1 | 12/2005 | Gordon |
| 2005/0278026 A1 | 12/2005 | Gordon |
| 2005/0283244 A1 | 12/2005 | Gordon |
| 2005/0283245 A1 | 12/2005 | Gordon |
| 2006/0004453 A1 | 1/2006 | Bartish, Jr. et al. |
| 2006/0015184 A1 | 1/2006 | Winterbottom et al. |
| 2006/0058878 A1 | 3/2006 | Michelson |
| 2006/0084986 A1 | 4/2006 | Grinberg et al. |
| 2006/0122701 A1 | 6/2006 | Kister |
| 2006/0129244 A1 | 6/2006 | Ensign |
| 2006/0142859 A1 | 6/2006 | Mcluen |
| 2006/0149385 A1 | 7/2006 | Mckay |
| 2006/0195192 A1 | 8/2006 | Gordon et al. |
| 2006/0229729 A1 | 10/2006 | Gordon |
| 2006/0241770 A1 | 10/2006 | Rhoda et al. |
| 2006/0253201 A1 | 11/2006 | Mcluen |
| 2007/0043442 A1 | 2/2007 | Abernathie |
| 2007/0050030 A1 | 3/2007 | Kim |
| 2007/0050032 A1* | 3/2007 | Gittings ............... A61F 2/4425 623/17.13 |
| 2007/0055377 A1 | 3/2007 | Hanson et al. |
| 2007/0191951 A1 | 8/2007 | Branch |
| 2007/0255415 A1 | 11/2007 | Edie et al. |
| 2007/0270963 A1 | 11/2007 | Melkent et al. |
| 2007/0270968 A1 | 11/2007 | Baynham |
| 2008/0021559 A1 | 1/2008 | Thramann |
| 2008/0065222 A1 | 3/2008 | Hamada |
| 2008/0077242 A1* | 3/2008 | Reo ............... A61F 2/442 623/17.15 |
| 2008/0077244 A1* | 3/2008 | Robinson ............... A61F 2/442 623/17.15 |
| 2008/0114467 A1 | 5/2008 | Capote et al. |
| 2008/0140207 A1 | 6/2008 | Olmos et al. |
| 2008/0147194 A1 | 6/2008 | Grotz et al. |
| 2008/0161933 A1 | 7/2008 | Grotz et al. |
| 2008/0167657 A1 | 7/2008 | Greenhalgh |
| 2008/0183204 A1 | 7/2008 | Greenhalgh et al. |
| 2008/0221694 A1 | 9/2008 | Warnick et al. |
| 2008/0275455 A1 | 11/2008 | Berry et al. |
| 2008/0281346 A1 | 11/2008 | Greenhalgh et al. |
| 2008/0288073 A1 | 11/2008 | Renganath et al. |
| 2008/0300598 A1 | 12/2008 | Barreiro et al. |
| 2008/0306488 A1 | 12/2008 | Altarac et al. |
| 2008/0319487 A1 | 12/2008 | Fielding et al. |
| 2008/0319549 A1 | 12/2008 | Greenhalgh et al. |
| 2009/0024217 A1 | 1/2009 | Levy et al. |
| 2009/0062833 A1 | 3/2009 | Song |
| 2009/0076616 A1 | 3/2009 | Duggal et al. |

(56) References Cited

U.S. PATENT DOCUMENTS

| | | |
|---|---|---|
| 2009/0125062 A1 | 5/2009 | Arnin |
| 2009/0149956 A1 | 6/2009 | Greenhalgh et al. |
| 2009/0149959 A1 | 6/2009 | Conner et al. |
| 2009/0204218 A1 | 8/2009 | Richelsoph |
| 2009/0222100 A1 | 9/2009 | Cipoletti et al. |
| 2009/0240334 A1 | 9/2009 | Richelsoph |
| 2009/0270989 A1 | 10/2009 | Conner et al. |
| 2009/0281628 A1 | 11/2009 | Oglaza et al. |
| 2009/0292361 A1 | 11/2009 | Lopez |
| 2009/0299478 A1 | 12/2009 | Carls et al. |
| 2009/0312763 A1 | 12/2009 | McCormack |
| 2010/0049324 A1 | 2/2010 | Valdevit |
| 2010/0070041 A1 | 3/2010 | Peterman |
| 2010/0082109 A1 | 4/2010 | Greenhalgh et al. |
| 2010/0145455 A1 | 6/2010 | Simpson et al. |
| 2010/0179657 A1 | 7/2010 | Greenhalgh et al. |
| 2010/0211176 A1 | 8/2010 | Greenhalgh |
| 2010/0222816 A1 | 9/2010 | Gabelberger et al. |
| 2010/0286783 A1 | 11/2010 | Lechmann et al. |
| 2011/0035011 A1 | 2/2011 | Cain |
| 2011/0093074 A1 | 4/2011 | Glerum et al. |
| 2011/0160861 A1 | 6/2011 | Jimenez et al. |
| 2011/0172774 A1 | 7/2011 | Varela |
| 2011/0276142 A1 | 11/2011 | Niemiec et al. |
| 2011/0301713 A1 | 12/2011 | Theofilos |
| 2011/0319996 A1* | 12/2011 | Barrall ............... A61F 2/442 623/17.12 |
| 2011/0319997 A1 | 12/2011 | Glerum et al. |
| 2012/0035729 A1 | 2/2012 | Glerum et al. |
| 2012/0059470 A1 | 3/2012 | Weiman |
| 2012/0059472 A1 | 3/2012 | Weiman |
| 2012/0109308 A1 | 5/2012 | Lechmann et al. |
| 2012/0116513 A1* | 5/2012 | Carpenter ........... A61F 2/4611 623/17.16 |
| 2012/0130496 A1 | 5/2012 | Duffield et al. |
| 2012/0165945 A1 | 6/2012 | Hansell et al. |
| 2012/0185049 A1 | 7/2012 | Varela |
| 2012/0209386 A1 | 8/2012 | Triplett et al. |
| 2012/0215313 A1 | 8/2012 | Saidha et al. |
| 2012/0226357 A1 | 9/2012 | Varela |
| 2012/0265309 A1 | 10/2012 | Glerum et al. |
| 2012/0277861 A1 | 11/2012 | Steele et al. |
| 2012/0277870 A1 | 11/2012 | Wolters et al. |
| 2012/0323329 A1 | 12/2012 | Jimenez et al. |
| 2012/0330426 A1 | 12/2012 | Mclaughlin et al. |
| 2013/0023993 A1 | 1/2013 | Weiman |
| 2013/0023994 A1 | 1/2013 | Glerum |
| 2013/0158663 A1 | 6/2013 | Miller et al. |
| 2013/0158669 A1 | 6/2013 | Sungarian et al. |
| 2013/0197647 A1 | 8/2013 | Wolters et al. |
| 2013/0211526 A1 | 8/2013 | Alheidt et al. |
| 2013/0274883 A1 | 10/2013 | McLuen et al. |
| 2014/0067071 A1 | 3/2014 | Weiman et al. |
| 2014/0088714 A1 | 3/2014 | Miller et al. |
| 2014/0163683 A1 | 6/2014 | Seifert et al. |
| 2015/0066145 A1 | 3/2015 | Rogers et al. |
| 2015/0088258 A1 | 3/2015 | Jimenez et al. |
| 2015/0134064 A1 | 5/2015 | Grotz et al. |
| 2015/0216676 A1 | 8/2015 | Shulock et al. |
| 2015/0289988 A1 | 10/2015 | Ashley et al. |
| 2015/0374508 A1 | 12/2015 | Sandul |
| 2016/0166396 A1 | 6/2016 | McClintock |
| 2016/0324654 A1 | 11/2016 | Loebl et al. |
| 2017/0100258 A1 | 4/2017 | Jimenez et al. |
| 2017/0119543 A1 | 5/2017 | Dietzel et al. |
| 2021/0059830 A1* | 3/2021 | Gross ............... A61F 2/4425 |

FOREIGN PATENT DOCUMENTS

| | | |
|---|---|---|
| DE | 4327054 C1 | 4/1995 |
| EP | 0576379 B1 | 6/1993 |
| EP | 0610837 B1 | 7/1994 |
| EP | 3111896 A1 | 1/2017 |
| FR | 2794968 A1 | 12/2000 |
| JP | 2000-513263 A | 10/2000 |
| KR | 200290058 Y1 | 9/2002 |
| SU | 1424826 A1 | 9/1988 |
| WO | 9201428 A1 | 2/1992 |
| WO | 9525485 A1 | 9/1995 |
| WO | 1999042062 A1 | 8/1999 |
| WO | 1999066867 A1 | 12/1999 |
| WO | 2002045625 A1 | 6/2002 |
| WO | 2004019829 A1 | 3/2004 |
| WO | 2004069033 A2 | 8/2004 |
| WO | 2006045094 A2 | 4/2006 |
| WO | 2006047587 A2 | 5/2006 |
| WO | 2006113080 A2 | 10/2006 |
| WO | 2008044057 A1 | 4/2008 |
| WO | 2008134515 A1 | 11/2008 |
| WO | 2009114381 A1 | 9/2009 |
| WO | 2010103344 A1 | 9/2010 |
| WO | 2012031267 A1 | 3/2012 |
| WO | 2015009793 A1 | 1/2015 |

* cited by examiner

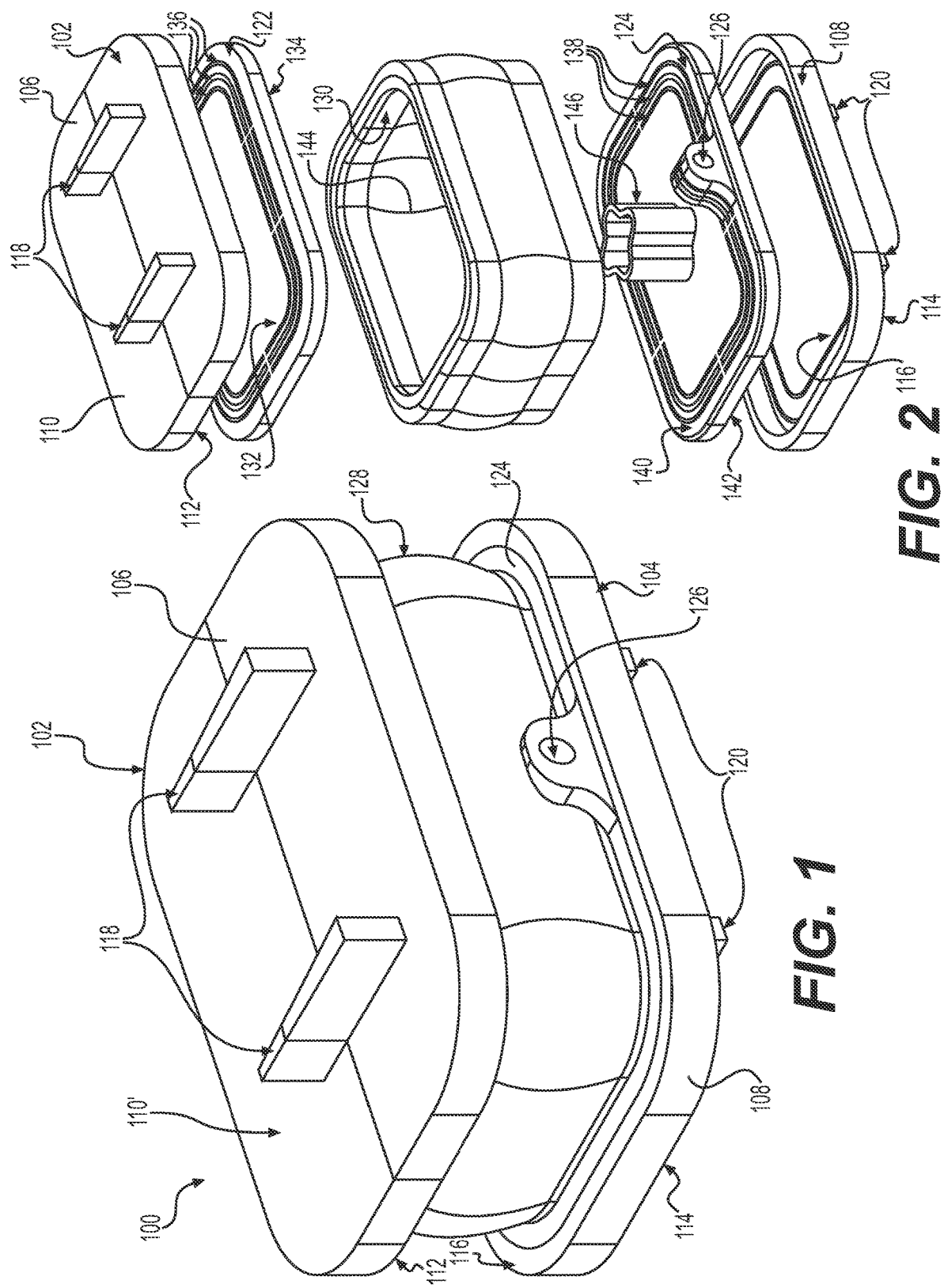

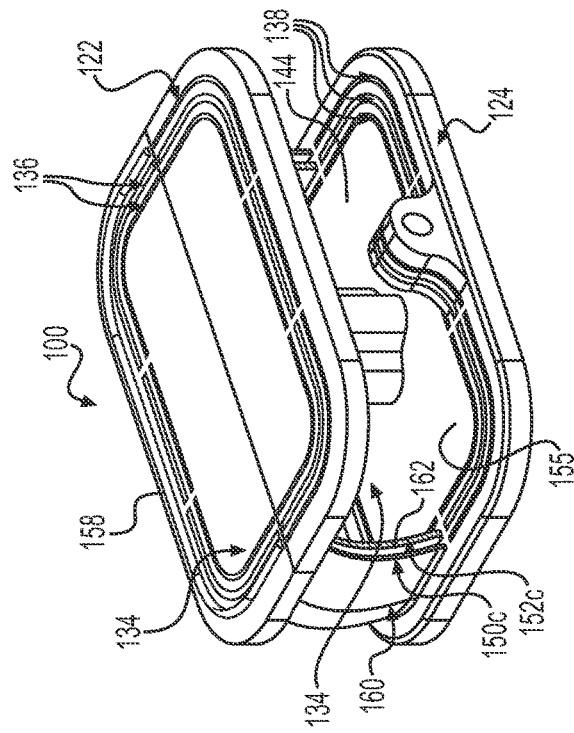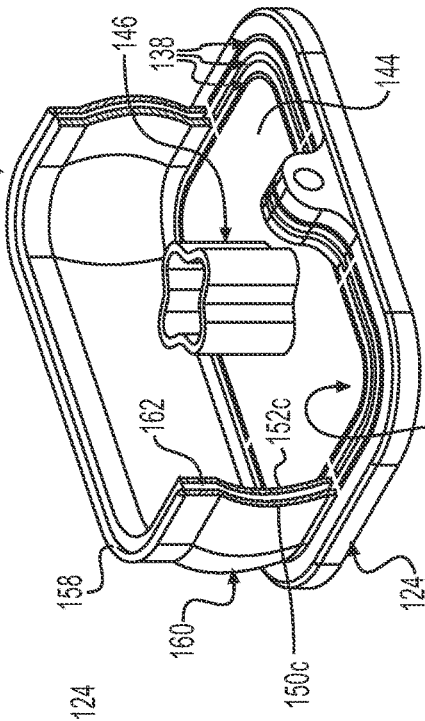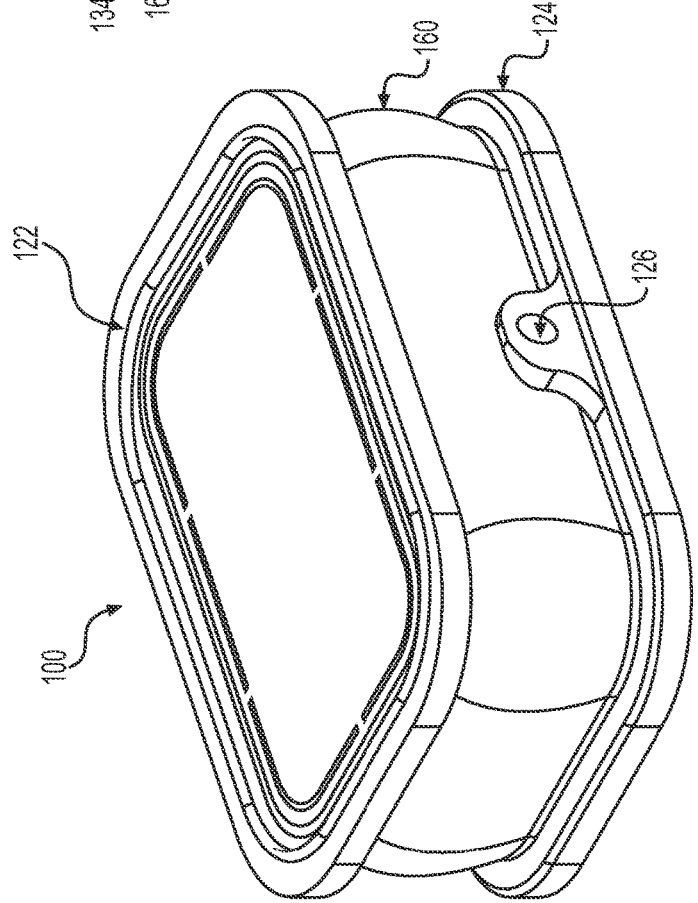

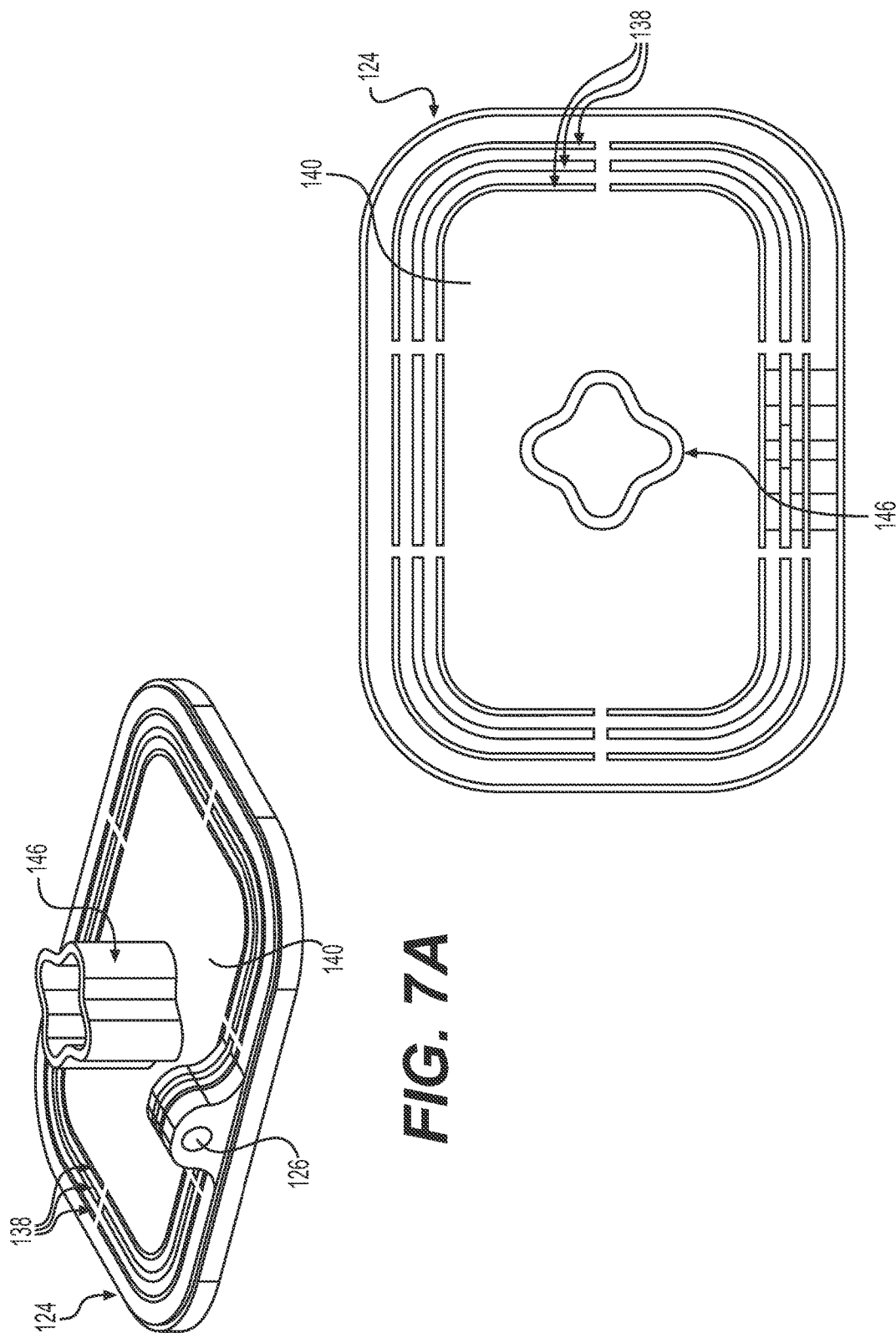

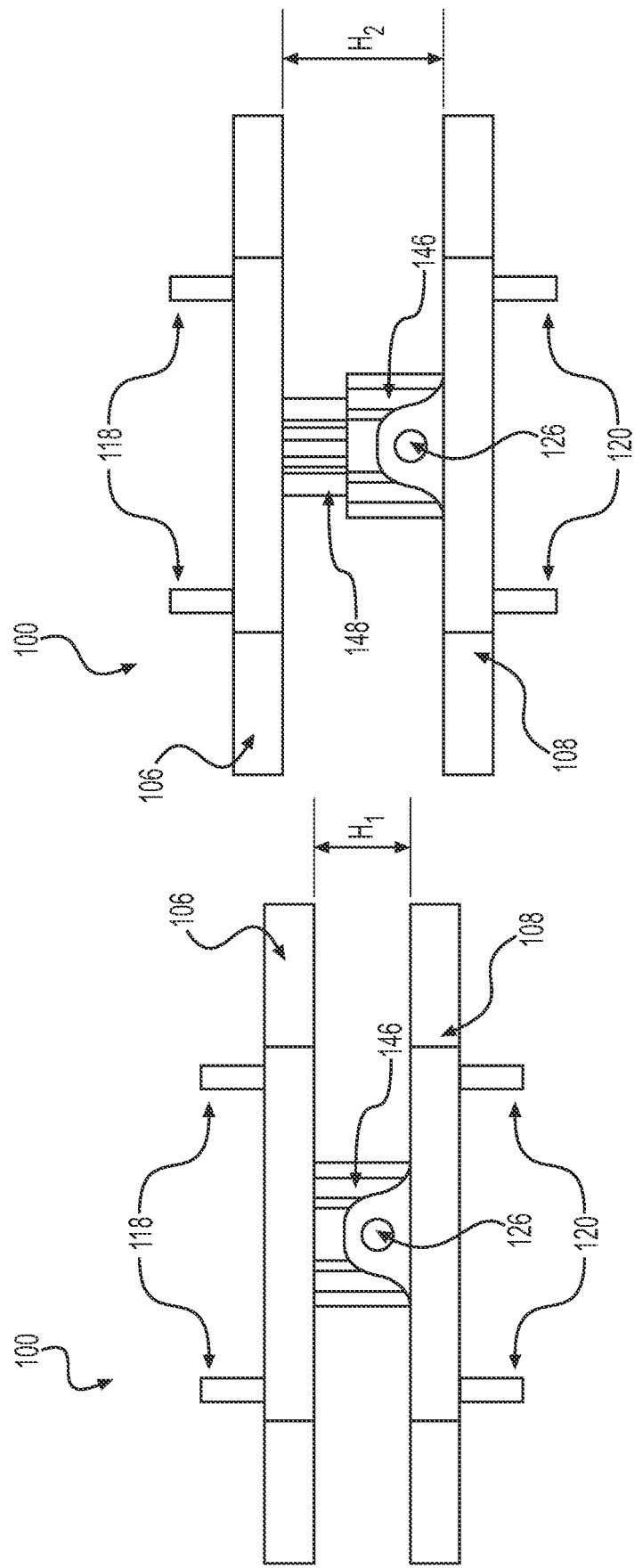

EXPANDABLE MOTION PRESERVATION SPACER

CROSS-REFERENCE TO RELATED APPLICATIONS

This application is a continuation of U.S. patent application Ser. No. 17/583,470 filed on Jan. 25, 2022 which is a continuation of U.S. patent application Ser. No. 16/563,084 filed on Sep. 6, 2019, which is incorporated in its entirety herein.

BACKGROUND

The vertebral or spinal column is a flexible assembly of vertebrae stacked on top of each other, extending from the skull to the pelvic bone, which acts to support the axial skeleton and to protect the spinal cord and nerves. The vertebrae are anatomically organized into four generalized body regions identified as cervical, thoracic, lumbar, and sacral. More specifically, the cervical region includes the top of the spine beginning at the skull; the thoracic region spans the torso; the lumbar region spans the lower back; and the sacral region includes the base of the spine, ending with the connection to the pelvic bone. With the exception of the first two cervical vertebrae, intervertebral discs, which are cushion-like discs, separate adjacent vertebrae.

The stability of the vertebral column during compression and movement is maintained by the intervertebral disc. The intervertebral disc primarily serves as a mechanical cushion permitting controlled motion between vertebral segments of the axial skeleton. The normal disc is a unique, mixed structure, comprised of three component tissues: the nucleus pulpous ("nucleus"), the annulus fibrosus ("annulus") and two vertebral end plates. The annulus and the nucleus are interdependent, as the annulus contains and secures the nucleus in place, and the nucleus aligns the annulus to accept/distribute external loads. The two vertebral end plates are composed of thin cartilage overlying a thin layer of hard, cortical bone which attaches to the spongy, richly vascular, cancellous bone of the vertebral body. The end plates thus act to attach adjacent vertebrae to the disc.

Many factors can adversely alter the composition and structure of the intervertebral disc, such as normal physiological aging, mechanical injury/trauma, and/or disease, resulting in impairment or loss of disc function. Mechanical injury can tear the annulus, allowing the gel-like material of the nucleus to extrude into the spinal canal and compress neural elements.

A common procedure for treating damage or disease of the spinal disc or vertebral body may involve partial or complete removal of an intervertebral disc. An implant, which may be referred to as an interbody spacer, can be inserted into the cavity created where the intervertebral disc was removed to help maintain height of the spine and/or restore stability to the spine. Conventional interbody spacers may be too large and bulky for introduction into the disc space in a minimally invasive manner, such as may be utilized in a posterior approach. Further, these conventional interbody spacers may have inadequate surface area contact with the adjacent endplates if sized for introduction into the disc space in a minimally invasive manner. In addition, conventional interbody spacers designed for introduction into the disc space in a minimally invasive manner may not allow motion preservation; thus, potentially not promoting the desired ease of more natural movement, expansion, and curvature of the spinal region.

SUMMARY

A first exemplary embodiment provides an expandable spacer that may comprise a first endplate; a second endplate spaced from the first endplate; and one or more bags disposed between the first endplate and the second endplate that couple the first endplate to the second endplate. The one or more bags may be configured to receive a filler material to expand the expandable spacer from an initial position having a first height to an expanded position having a second height, wherein the second height is greater than the first height.

Another exemplar embodiment provides an expandable spacer that may comprise a first endplate having an exterior side and an interior side, a first main plate seated in the interior side of the first endplate, a second endplate having an exterior side an interior side, a second main plate seated in the interior side of the second endplate, a plurality of bags disposed between the first main plate and the second main plate; and an injection port fixedly attached to the second main plate. The plurality of bags may couple the first main plate and the second main plate to one another. The plurality of bags may define a perimeter that forms a hole. The injection port may be configured to receive a filler material to expand the plurality of bags to place the expanded spacer in an expanded position.

Yet another example embodiment provides method that may comprise inserting an expandable spacer into a void between adjacent vertebrae; and injecting a filler material into the expandable spacer positioned in the void to cause one or more bags to expand and force apart a first endplate and a second endplate of the expandable spacer.

BRIEF DESCRIPTION OF THE DRAWINGS

These drawings illustrate certain aspects of some examples of the present disclosure, and should not be used to limit or define the disclosure, wherein:

FIG. 1 is a perspective view of an expandable motion preservation spacer shown in an expanded position in accordance with particular embodiments of the present disclosure;

FIG. 2 is an exploded view of the expandable motion preservation spacer of FIG. 1 in accordance with particular embodiments of the present disclosure;

FIGS. 5A, 5B, and 5C illustrate the configuration of a single bag in accordance with particular embodiments of the present disclosure;

FIGS. 7A and 7B illustrate a second main plate of an expandable motion preservation spacer in accordance with particular embodiments of the present disclosure; and FIGS. 8A and 8B illustrate a connected first endplate and second endplate of an expandable motion preservation spacer in accordance with particular embodiments of the present disclosure.

DETAILED DESCRIPTION

Figure 3:
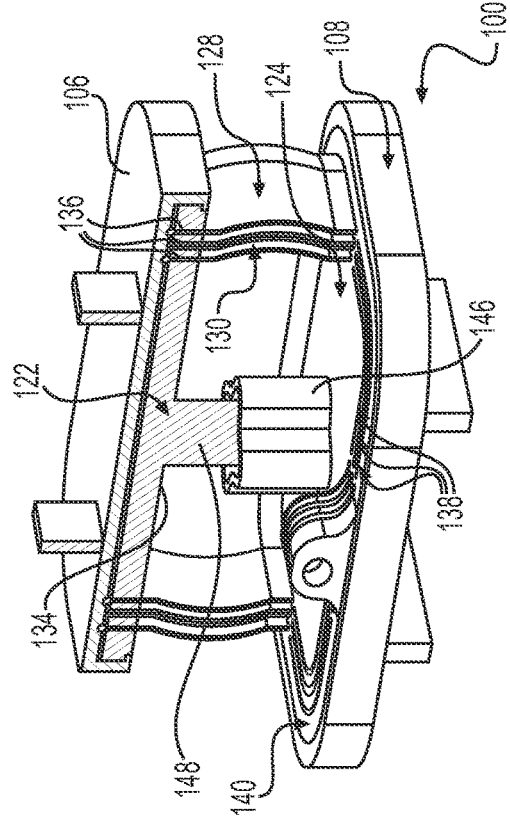
FIG. 3 is a cross-sectional view of the expandable motion preservation spacer of FIG. 1 shown in an expanded position in accordance with particular embodiments of the present disclosure.

Particular embodiments disclosed herein generally relate to spacers for use in orthopedic treatments, particularly to implants for insertion between two adjacent bony structures or two adjacent joint surfaces, and more particularly relate to an expandable spacer for insertion into the void remaining in the intervertebral space after removal of damaged disc material.

In accordance with particular embodiments, the expandable spacer disclosed herein and methods for its insertion may be used in a treatment protocol for any condition in a patient involving diseased or damaged bony structures. The patient can be a human being. Additionally, it is contemplated that the expandable spacer may be useful in veterinary science for any animal having adjacent bony structures to be fused. The expandable spacer may be inserted into a space through a small incision and narrow pathways using appropriate minimally invasive techniques, positioned across the space, and expanded to the desired height. The incision may be short, for example, about one inch in length, smaller than the implant in an expanded configuration. If the desired position and/or expansion are not achieved, the expandable spacer may be collapsed, repositioned, and expanded in situ.

FIG. 1 is a perspective view of an expandable spacer 100 shown in an expanded position in accordance with some embodiments of the present disclosure. In the embodiment depicted, the expandable spacer 100 includes a first side 102 and a second side 104, wherein a first endplate 106 may be situated at the first side 102, and wherein a second endplate 108 may be situated at the second side 104. The first endplate 106 may have an exterior side 110 and an interior side 112. Similarly, the second endplate 108 may also have an exterior side 114 and an interior side 116. The exterior sides 110, 114 of the first and second endplates 106, 108 may include a plurality of protrusions 118, 120 affixed thereto. Although not shown in FIG. 1, the interior side 112 of the first endplate 106 may be configured so that a first main plate 122 (e.g., shown on FIG. 2) may be seated therein. Similarly, the second endplate 108 may be configured so that a second main plate 124 may be seated therein. The second main plate 124 may include an injection port 126 fixedly attached thereto. One or more bags (e.g., first bag 128) may be positioned between the first main plate 122 (not shown in FIG. 1) and the second main plate 124.

In accordance with particular embodiments, the expandable spacer 100 allows for separation of the first endplate 106 from the second endplate 108 by injecting a filler material into the one or more bags (e.g., first bag 128) and/or a hole formed inside the one or more bags (e.g. hole 144 on FIG. 2). By way of example, the filler material may be injected through the injection port 126 disposed on the second main plate 124. Injection of the filler material may facilitate expansion of the expandable spacer 100 from an initial position (e.g., closed or compressed) to an expanded position based, for example, on the amount of filler material injected. Suitable filler materials may include a synthetic or natural nucleus material including, but not limited to, a saline solution, silicone gel, poly(dimethylsiloxane) (PDMS) or Low MW poly(dimethylsiloxane), Poly(ethyleneoxide-copropyleneoxide)(PEO-PPO), Poly(vinylalcohol). The one or more bags (e.g., first bag 128) may connect the first and second endplates 106, 108, thereby ensuring capsulation of the filler material at a designed pressure. The pressure may be about 0.1 MPa to about 1.5 MPa. Alternatively, the pressure may be about 0.05 MPa to about 5 MPa, about 0.01 MPa to about 10 MPa.

In some embodiments the expandable spacer 100 may be expanded parallel or with a lordotic angle, depending on how the one or more bags (e.g., first bag 128) are attached to the first endplate 106 and/or the second endplate 108. Particular embodiments of the expandable spacer 100 may have an initial position (e.g., a closed or compressed form) and an expanded position. The initial position may have an initial height and lordosis. For example, the initial position may have a height of about 4 mm to about 10 mm. Alternatively, the initial position may have a height of about 4 mm to about 10 mm, about 5 mm to about 9 mm, about 6 mm to about 8 mm. The initial position may have an initial lordosis of about 0 degrees to about 6 degrees. Alternatively, the initial position may have a lordosis of about 0 degrees to about 6 degrees, about 1 degree to about 5 degrees, or about 2 degrees to about 4 degrees.

Embodiments disclosed herein may be expanded to a predefined parallel or lordotic forms. The expanded position of the expandable spacer may have a height of about 5 mm to about 15 mm. Alternatively, the expanded position of the expandable spacer may have a height of about 6 mm to about 14 mm, about 7 mm to about 13 mm, or about 8 mm to about 12 mm. The expanded position of the expandable spacer may have a lordosis of about 4 degrees to about 10 degrees, about 5 degrees to about 9 degrees, or about 6 degrees to about 8 degrees. At maximum height, some embodiments disclosed herein may include a mechanism, such as a stop, to prevent the first and second endplates from sliding freely. This is a safety feature, ensuring the safe operation of the expandable spacer 100 at its maximum height.

Any one or all of the members of the expandable spacer 100 may be made from any suitable biocompatible material, including synthetic or natural autograft, allograft or xenograft tissues, and may be resorbable or non-resorbable in nature, Examples of tissue materials include hard tissues, connective tissues, demineralized bone matrix, and combinations thereof. Further examples of resorbable materials are polylactide, polyglycolide, tyrosine-derived polycarbonate, polyanhydride, polyorthoester, polyphosphazene, calcium phosphate, hydroxyapatite, bioactive glass, and combinations thereof. Further examples of non-resorbable materials are non-reinforced polymers, carbon-reinforced polymer composites, PEEK and PEEK composites, shape-memory alloys, titanium, titanium alloys, cobalt chrome alloys, stainless still, ceramics, and combinations thereof, as well as others.

The expandable spacer 100 may be manufactured using any method for making similar objects. Particularly applicable are methods for molding plastics, for example, injection molding or blow molding. Also applicable are methods for cutting metal and/or for making metal parts, for example, shearing, laser cutting apparatus, and waterjets. The implant may be manufactured as a whole or fabricated from individual parts. The parts may be snapped or welded together in a number of different ways.

After assembly, the expandable spacer 100 may be sterilized and packaged. Sterilization may be accomplished by autoclave, ultraviolet lamp, bleach solutions, alcohol solutions, and/or combinations thereof. The expandable spacers may be packaged individually or in groups, using any material suitable for packaging medical items.

Methods for using the expandable spacer 100 are also disclosed herein. Although methods disclosed herein are suitable for fusion of vertebrae, the expandable spacer 100 may also be suitable for fusion of any adjacent bones or joints, such as the ankle or knee. The methods may not be limited to the embodiments described herein.

After anesthetizing the patient, a surgical incision may be made to access the two adjacent vertebrae to be fused in the patient's body. The surgeon may use a posterior approach, anterior approach, lateral approach, or any other approach deemed appropriate for the patient. The accessed space between the vertebrae may be prepared for insertion of the expandable spacer 100. The surgeon may do one or more of the following: discectomy, dissect and remove bone, and reposition or remove cartilage, including removal of all or part of the vertebral endplates and/or cortical bone. The expandable spacer 100 may then be inserted into the prepared space using any suitable technique, for example, the expandable spacer 100 can be inserted to the space through a cannula in an initial form. In some embodiments, the insertion may be monitored, for example, using an endoscope. After insertion, the filler material may be injected into the one or more bags (e.g., first bag 128). As the filler material is injected, the bags should expand causing the first endplate 106 and the second endplate 108 to move away from one another other, resulting in expansion of the expandable spacer 100.

In order to expose the cancellous bone, removal of all or part of the vertebral endplates and cortical bone layer can be done. In some embodiments, the expandable spacer 100 may be in contact with the bone marrow as the bone marrow provides osteoprogenitor cells which enhance the growth and formation of new bone. When proper distraction is achieved, the expandable spacer 100 may be adjusted to a therapeutically acceptable height for the patient. A "therapeutically-acceptable" height may be any height that provides beneficial to the patient, e.g., reduced pain, reduced pressure on nerve roots, restoration of joint function, restoration of motion, and/or repair of diseased or injured condition. The expandable spacer 100 may be collapsed and reextended if necessary, for a better fit if the insertion is not secure or the height may be incorrect, or a condition in the patient changes.

Moreover, after surgery if the expandable spacer 100 needs any readjusting or repositioning, the expandable spacer 100 may be accessed and adjusted via a minimally invasive procedure. Thus, the need for replacement of the expandable spacer 100 may be decreased, and in turn, decreasing pain and costs for the patient may be realized. Although the expandable spacer 100 may not require any supplemental fixation with devices such as rods, screws, and additional plates, these devices may be ultimately used. When the expandable spacer is positioned and secured in the desirable manner, the surgical incision may be closed, and the patient may be allowed to heal.

FIG. 2 is an exploded view of the expandable spacer 100 of FIG. 1 in accordance with some embodiments of the present disclosure. As depicted, the expandable spacer 100 may include a first endplate 106, a first main plate 122, a first bag 128, a second bag 160, a second main plate 124, and a second endplate 108. As depicted, the first main plate 122 may be coupled to the first endplate 106. For example, the interior side 112 of the first endplate 106 may be configured so that the first main plate 122 may be seated therein. The first main plate 122 may include an exterior side 132 and an interior side 134. In some embodiments, grooves 136 may be disposed at or around the perimeter of the first main plate 122. The first and second bags 128, 130 may be configured to be seated in the grooves 136 formed in the first main plate 122. As depicted, the second main plate 124 may be coupled to the second endplate 108. For example, the interior side 116 of the second endplate 108 may be configured so that the second main plate 124 may be seated therein. The second main plate 124 includes an interior side 140 and an exterior side 142, wherein a housing 146 may be affixed at or near the center thereof, on the interior side 140. Although not shown in FIG. 2, the housing 146 may be configured to receive, by slidable engagement, an extension 148 (e.g., FIGS. 3 and 6A) from the interior side 134 of the first main plate 122. In some embodiments, grooves 138 may be disposed at or around the perimeter of the second main plate 124. The first and second bags 128, 130 may be configured to be seated in the grooves formed in the second main plate 124. Both the first and second endplates 106, 108 may have protrusions 118, 120 disposed on their exterior sides 110, 114.

As depicted, the one or more bags (e.g., the first and second bags 128, 130) may define a perimeter that defines a hole 144. In some embodiments, the first and second bags 128, 130 may be concentric. For example, the second bag 160 may be placed inside the first bag 128 with the first bag 128 defining a perimeter that surrounds the second bag 160. The one or more bags (e.g., first and second bags 128, 130) may be constructed from any suitable material. Suitable materials may include, for example, polytetrafluoroethylene (PTFE), extended-PTFE, Poly(propylene) (PP), Poly(ethylene terphthalate) (PET). The one or more bags (e.g., first and second bags 128, 130) may have any suitable shape. For example, suitable shapes may include, but are not limited to, toroids, polyhedrons, and variations thereof. In some embodiments, the suitable shape may include a polyhedron with rounded corners and/or edges. In some embodiments, the suitable shape may include an annular shape with straight side and rounded corners and/or edges. In some embodiments, the suitable shape may define a perimeter defining the hole 144.

FIG. 3 is a cross-sectional view of the expandable spacer 100 of FIG. 1 in accordance with particular embodiments shown in an expanded position. As depicted in FIG. 3, the expandable spacer 100 may include a first plate 102 and a second plate 116 connected by first and second bags 128, 130. As previously described, the first and second bags 128, 130 may be secured in the grooves 136 formed in the first main plate 122 and also secured in the grooves 138 formed in the second main plate 124. As depicted, the first main plate 122 may include an extension 148 from the interior side 134. In some embodiments, the extension 148 may be received in a housing 146 that extends from an interior side 140 of the second main plate 124. In some embodiments, the housing 146 may be configured to receive the extension 148 by slidable engagement. By securing the extension 148 in the housing 146 expansion of the expandable spacer 100 may be controlled, reducing the tendency of the first plate 102 and the second plate 116 from becoming misaligned during expansion.

Figure 4B:
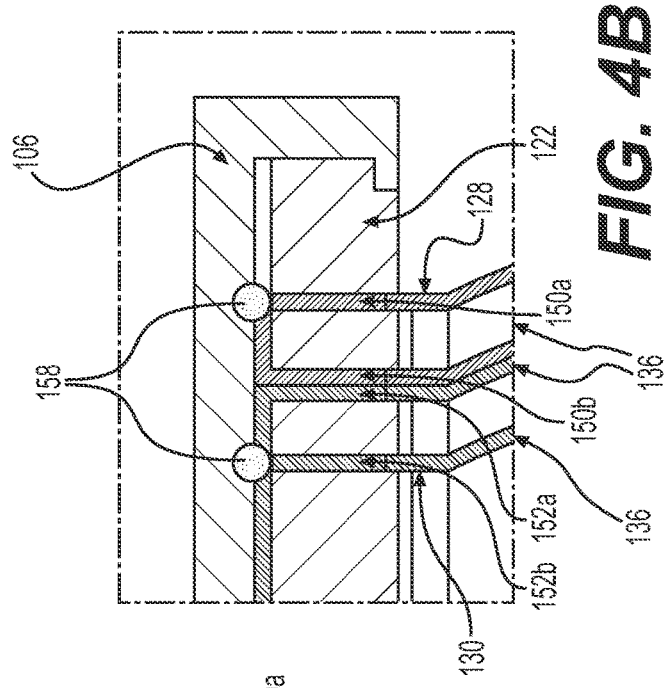
FIG. 4B is a close-up view of FIG. 4A taken along box 4B in accordance with particular embodiments of the present disclosure.
Figure 4A:
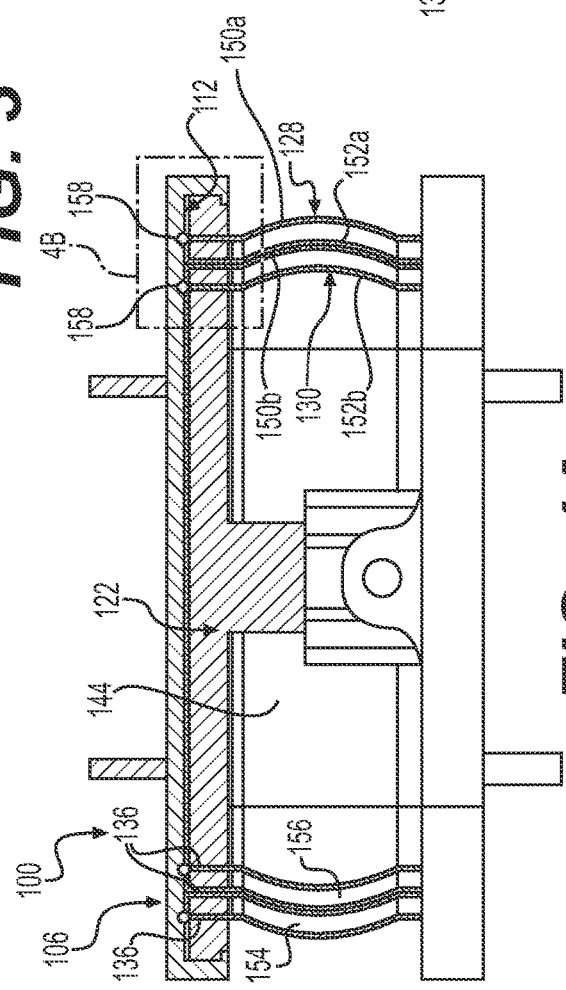
FIG. 4A illustrates a front cross-sectional view of the expandable motion preservation spacer of FIG. 1 shown in an expanded position in accordance with particular embodiments of the present disclosure.

FIGS. 4A and 4B illustrate a front cross-sectional view of the expandable spacer 100 of FIG. 1 shown in an expanded position. FIG. 4A is a front cross-sectional view of the expandable spacer 100 of FIG. 1 shown in an expanded position. FIG. 4B is an enlarged view of FIG. 4A taken along box 4B. As depicted, the one or more bags (e.g., first bag 128 and second bag 160) may include multiple skins, shown as first outer skin 150a, second outer skin 150b, first inner skin 152a, and second inner skin 152b. By way of example, the first bag 128 may include a first outer skin 150a and a first inner skin 152a. The first outer skin 150a and the first inner skin 152a may define a first interior volume 154 of the first bag 128 that receives the filler material for filling and expanding the first bag 128. By way of further example, the second bag 160 may include a second outer skin 150b and a second inner skin 152b. The second inner skin 150b and the second inner skin 152b may define a second interior volume 156 for receiving the filler material for filling and expanding the second bag 160. The second bag 160 may also formed a perimeter defining hole 144 that can also receive the filler material. Thus, the filler material may be introduced into the hole 144, the first interior volume 154, and/or the second interior volume 156.

In some embodiments, the first outer skin 150a and first inner skin 152a may be secured to one another to form the first bag 128 and the second outer skin 150b and the second inner skin 152b may be secured to one another to form the second bag 160. Any suitable technique may be used for securing the skins to one another for forming the first and second bags 128, 130, respectively. Suitable techniques may include, for example, adhesives, stitching, or heat melding among others. In some embodiments, the first outer skin 150a and the first inner skin 152a may extend upward through the grooves 136 in the first main plate 122 and may be further secured in place with stitches 158. The stitches 158 may hold the first inner outer skin 150a the first outer skin 112 together forming the first bag 128. In some embodiments, the second outer skin 150b and the second inner skin 152b may extend upward through the grooves 136 in the first main plate 122 and may be further secured in place with stitches 158. The stitches 158 may hold the second outer skin 150a the second outer skin 112 together forming the first bag 128. As depicted, the stitches 158 for both the first bag 128 and the second bag 160 may be disposed between the first plate 102 and the first main plate 122. The stitches 158 may be made from any suitable material. For example, the stitches 158 may comprise a biocompatible material, such as Poly(propylene) (PP), Poly(ethylene terphthalate) (PET) or Poly(tetrafluroethylene) (PTFE). While the preceding description describes use of separate skins (e.g., first outer skin 150a and first inner skin 152a) for forming the one or more bags, it should be understood that that the bags (e.g., first bag 128 and second bag 160) may be otherwise formed. For example, the one or more bags may each be formed from a continuous skin. In addition, while separate bags (e.g., first bag 128 and second bag 160) are shown, the one or more bags may be a single bag that is configured to define one or more interior volumes (e.g., first interior volume 154, second interior volume 156, etc.) for receiving the filler material.

FIGS. 5A, 5B, and 5C illustrate another embodiment of the expandable spacer 100 that utilize a single bag 160. FIG. 5A is a perspective view of the expandable spacer 100 showing a single bag 160. As depicted, the expandable spacer may include a first main plate 122, a second main plate 124, and first bag 128. For simplicity, the first plate 102 (e.g., shown on FIG. 1) and the second plate 116 (e.g., shown on FIG. 1) are not depicted on FIG. 5A. As depicted in FIG. 5A, the single bag 160 may be disposed between the first main plate 102 and the second main plate 124. In some embodiments, the injection port 126 on the second main plate 124 allows for the injection of filler material into the expandable spacer 100, for example, into the single bag 160 and/or the hole 144 defined by the single bag 160.

Referring to FIGS. 5B and 5C, partial cross-sectional views of the expandable spacer 100 of FIG. 5A are shown, in accordance with particular embodiments of the present disclosure. In FIG. 5C, the expandable spacer 100 is shown without the top main plate 122 for simplicity. As depicted in FIGS. 5B and 5C, the single bag 160 may include a first outer skin 150c and a first inner skin 152c. As depicted, the first outer skin 150c and the first inner skin 152c define an interior volume 162 of the single bag 160 that can be filled with a filler material for expansion of the single bag 160, thereby expanding the expandable spacer 100. In some embodiments, the first outer skin 150c and the second outer skin 152c may extend into grooves 136 formed in the first main plate 122. With specific reference to FIG. 5B, the first outer skin 150c and the second outer skin 152c may extend through the exterior side 132 of the first main plate 122 with stitches 158 securing the first outer skin 150c and the second outer skin 152c to one another. At the second main plate 124, the single bag 160 may be secured in grooves 138 formed in the second main plate 124. For example, the first outer skin 150c and the second outer skin 112 may extend into and be secured in the grooves 138 in the second main plate 124. The second main plate 124 may also include a housing 146 that extends from an interior side 140 and is configured to receive the connector 126 from the first main plate 122.

Figures 6A, 6B:
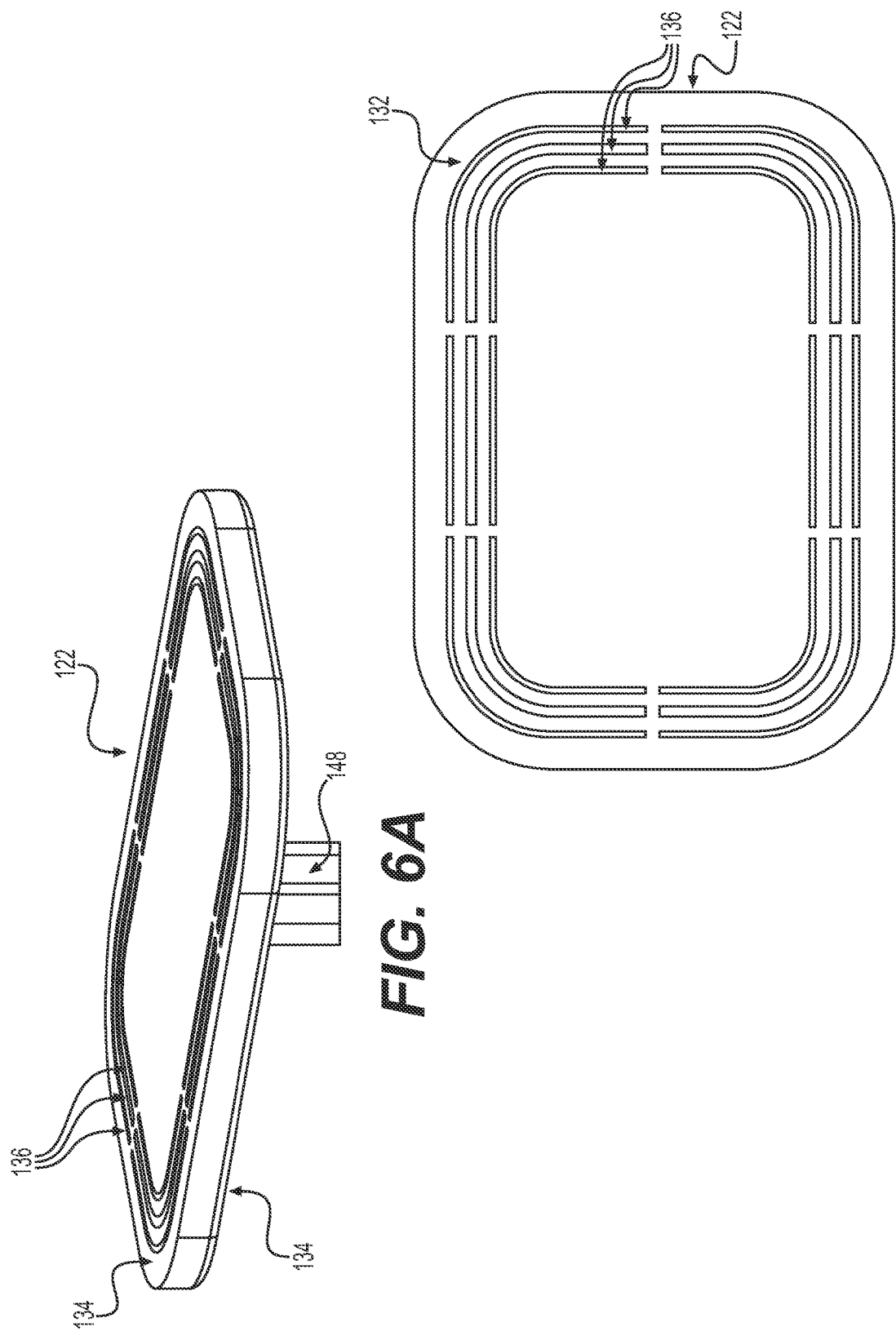
FIGS. 6A and 6B illustrate the first main plate of an expandable motion preservation spacer in accordance with particular embodiments of the present disclosure.

FIGS. 6A and 6B illustrate a first main plate 122 of an expandable spacer 100 (e.g., shown on FIG. 1) in accordance with particular embodiments of the present disclosure. FIG. 6A is a perspective view of the first main plate 122 in accordance with particular embodiments. FIG. 6B is a top plan view of the first main plate 122 in accordance with particular embodiments. As shown in FIG. 6A, the first main plate 122 may include grooves 136 disposed at or near the perimeter thereof, on the exterior side 132. As depicted, the grooves 136 may be radially spaced. As previously described, the grooves 136 may receive skins (e.g., first outer skin 150a shown on FIG. 4A, first inner skin 150a shown on FIG. 4A, etc.) that form the one or more bags (e.g., first bag 128 on FIG. 1). While obstructed from view on FIGS. 6A and 6B, the grooves may extend through the exterior side 132 to the interior side 134. The number of grooves 136 may be selected, for example, based on the number of the one or more bags required for a specific application. Moreover, also depicted is the extension 148 that may be disposed on the interior side 134 of the first main plate 122, where the extension 148 may be attached at or near the center thereof. For the embodiment shown, the extension 148 may be slidably connected to the housing 146 (e.g., shown on FIG. 7A). The extension 148 may be a variety of shapes and sizes, depending upon the specific procedure.

FIGS. 7A and 7B illustrate a second main plate of an expandable spacer 100 (e.g., shown on FIG. 1) in accordance with particular embodiments of the present disclosure. FIG. 7A is a perspective view of the second main plate 124 in accordance with particular embodiments. FIG. 7B is a top plan view of the second main plate 124 in accordance with particular embodiments. As shown, the second main plate 124 may include grooves 138 disposed at or near the perimeter thereof. As depicted, the grooves 138 may be radially spaced. As previously described, the grooves 138 may receive skins (e.g., first outer skin 150a shown on FIG. 4A, first inner skin 152a shown on FIG. 4A, etc.) that form the one or more bags (e.g., first bag 128 on FIG. 1). The number of grooves 138 may selected, for example, based on the number of the one or more bags required for a specific application. Moreover, also depicted is the housing 146 that may extend from the interior side 140 of the second main plate 124, where the housing 146 may be attached at or near the center thereof. For the embodiment shown, the housing 146 may be slidably connected to the extension 148 (e.g., shown on FIGS. 6A and 6B). The housing 146 may be a variety of shapes and sizes, allowing for slidable connection with the extension 148. Also shown in FIG. 7A is the injection port 126, whereby the injection port 126 may be fixedly attached to the second main plate 124. The injection port 126 allows injection of the filler material into the one or more bags (e.g., first bag 128 on FIG. 1) for expansion of the expandable spacer 100. In some embodiments, the injection port 126 may be sealed by a screw or similar attachment device (not shown).

FIGS. 8A and 8B illustrate a connected first endplate 106 and second endplate 108 of an expandable spacer 100 in accordance with particular embodiments of the present disclosure. FIG. 8A is a front plan view of the first endplate 106 and the second endplate 108 of the expandable motion preservation spacer 100 in a collapsed position. FIG. 8B is a front plan view of the first endplate 106 and the second endplate 108 of the expandable spacer 100 in an expanded position. In the embodiment shown, the one or more bags (e.g., first bag 128 shown on FIG. 1) are not depicted for the purpose of showing the expansion area of the expandable spacer 100. The expandable spacer 100 may be suitable for insertion into a patient's intervertebral space to restore the height and shape of the space.

As depicted, the expandable spacer 100 has a first height H1 in the collapsed position (e.g., see FIG. 8A) and a second height H2 in the expanded position (e.g., see FIG. 8B). In an initial position (or compressed position), for example, the extension 148 may be seated completely inside of the housing 146. After the injection of the filler material into the injection port 126, the filler material may flow into the expandable spacer 100. The introduction of the filler material into the expandable spacer 100 should result in expansion of the one or more bags (e.g., first bag 128 and second bag 160 shown on FIG. 2). Subsequently, the one or more bags may vertically lift causing the first and second endplates 106, 108 to move away from another and expand the expandable spacer 100. From the initial position shown in FIG. 8A, the expansion may cause the first and second endplates 106, 108 to move away from one another. In its expanded position, as depicted in FIG. 8B, the extension 148 may no longer be completely seated within the housing 146. Moreover, in addition to providing flexible movement along the vertical axis, the expandable spacer 100 may also be capable of movement in the horizontal direction, therefore allowing for flexible side-to-side and back- and forth movement. Thus, the expandable spacer 100 may provide for more natural vertebral movement.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. An expandable spacer comprising:
a first endplate;
a first base plate that is received in the first endplate;
a second endplate spaced from the first endplate;
a second base plate that is received in the second endplate; and
one or more bags disposed between the first endplate and the second endplate that couple the first endplate to the second endplate;
wherein the one or more bags are configured to expand the expandable spacer from an initial position having a first height to an expanded position having second height, wherein the second height is greater than the first height, and
wherein the first base plate comprises an extension from an interior side of the first base plate, and wherein the second base plate comprises a housing that extends from an interior side of the second plate and that slidably receives the extension from the first base plate.

2. The expandable spacer of claim 1, wherein the one or more bags are secured to the first base plate.

3. The expandable spacer of claim 2, wherein the one or more bags each comprise an inner layer and an outer layer that extend through grooves formed in the first base plate, the inner layer and the outer layer being secured to one another by stitches disposed between the first base plate and the first endplate.

4. The expandable spacer of claim 1, wherein the one or more bags are secured to the second base plate.

5. The expandable spacer of claim 1, further comprising a first base plate coupled to the first endplate and a second base plate coupled to the second endplate, wherein the one or more bags are secured to the first base plate and the second base plate.

6. The expandable spacer of claim 1, wherein the one or more bags form a perimeter that defines a hole.

7. The expandable spacer of claim 6, wherein the one or more bags comprise a first bag and second bag that are concentric, wherein the first bag and the second bag each individually comprise an internal layer and an external layer.

8. The expandable spacer of claim 1, wherein the one or more bags are generally annular in shape.

9. The expandable spacer of claim 1, wherein the initial height is about 2 mm to about 10 mm, and wherein the second height is about 8 mm to about 14 mm.

10. The expandable spacer of claim 1, wherein the initial position of the expandable spacer has a lordosis of about 0 degrees to about 6 degrees, and wherein the expanded position has a lordosis of about 4 degrees to about 10 degrees.

11. An expandable spacer comprising:
a first endplate having an exterior side and an interior side;
a first main plate seated in the interior side of the first endplate;
a second endplate having an exterior side and an interior side;
a second main plate seated in the interior side of the second endplate;
a plurality of bags disposed between the first main plate and the second main plate that couple the first main plate and the second main plate to one another, wherein the plurality of bags defines a perimeter that forms a hole; and
an injection port fixedly attached to the second main plate and configured to expand the plurality of bags to place the expanded spacer in an expanded position,
wherein the plurality of bags each comprise an inner layer and an outer layer that extend through grooves formed in the first main plate, the inner layer and the outer layer being secured to one another by stitches disposed between the first base plate and the first endplate.

12. The expandable spacer of claim 11, wherein the first main plate comprises an extension from an interior side of the first main plate, and wherein the second main plate comprises a housing that extends from an interior side of the second main plate and that slidably receives the extension from the first base plate.

13. The expandable spacer of claim 11, wherein the plurality of bags comprises a first bag and second bag that are concentric, wherein the first bag and the second bag each individually comprise an internal layer and an external layer.

14. The expandable spacer of claim 11, wherein the expandable spacer has an initial height of about 2 mm to about 10 mm, and wherein the expandable spacer has a second height in the expanded position of about 8 mm to about 14 mm.

15. The expandable spacer of claim 14, wherein an initial position of the expandable spacer has a lordosis of about 0 degrees to about 6 degrees.

16. The expandable spacer of claim 14, wherein the expanded position of the expandable spacer has a lordosis of about 4 degrees to about 10 degrees.

* * * * *